US010695552B2

(12) United States Patent
     Tu

(10) Patent No.: US 10,695,552 B2
(45) Date of Patent: Jun. 30, 2020

(54) WIRING LOOP STRUCTURE OF SKIN ELECTRODE PAD PRODUCTION MACHINE

(71) Applicant: Feng Ching Tu, Taipei (TW)

(72) Inventor: Feng Ching Tu, Taipei (TW)

( * ) Notice: Subject to any disclaimer, the term of this patent is extended or adjusted under 35 U.S.C. 154(b) by 607 days.

(21) Appl. No.: 15/366,582

(22) Filed: Dec. 1, 2016

(65) Prior Publication Data
    US 2018/0154134 A1    Jun. 7, 2018

(51) Int. Cl.
     *A61N 1/04*    (2006.01)
(52) U.S. Cl.
     CPC ............ *A61N 1/0492* (2013.01); *A61N 1/048* (2013.01)
(58) Field of Classification Search
     CPC ........ A61N 1/048; A61N 1/0492; H01R 4/04; H01R 32/28
     See application file for complete search history.

(56) References Cited

U.S. PATENT DOCUMENTS

| 4,409,981 A * | 10/1983 | Lundberg | A61B 5/0408 600/392 |
| 4,622,089 A * | 11/1986 | Lauritzen | A61F 13/0203 156/250 |
| 4,699,649 A * | 10/1987 | Rorer | A01N 47/36 504/212 |
| 4,838,273 A * | 6/1989 | Cartmell | A61B 5/04026 600/385 |
| 2015/0313499 A1 | 11/2015 | Sohn | |

* cited by examiner

*Primary Examiner* — Livius R. Cazan
(74) *Attorney, Agent, or Firm* — Muncy, Geissler, Olds & Lowe, P.C.

(57) ABSTRACT

A wiring loop structure of a skin electrode pad production machine includes a first transmission means for transmitting a strip clad substrate portion, a second transmission means for transmitting a strip conductive adhesive portion, a circulation conveyor belt with plural positioning fixtures, and two laminating rollers for laminating the clad substrate portion and the conductive adhesive portion. The first transmission means includes an assembling roller disposed above an end of the circulation conveyor belt, and the positioning fixture is provided for positioning an electrode lead, and the assembling roller strip clad is provided for adhering the substrate portion to the electrode lead, and the two laminating rollers are provided for attaching the strip clad substrate portion and the conductive adhesive portion after being laminated by the two laminating rollers, so as to facilitate the electrode lead to assemble and manufacture the electrode pad.

4 Claims, 5 Drawing Sheets

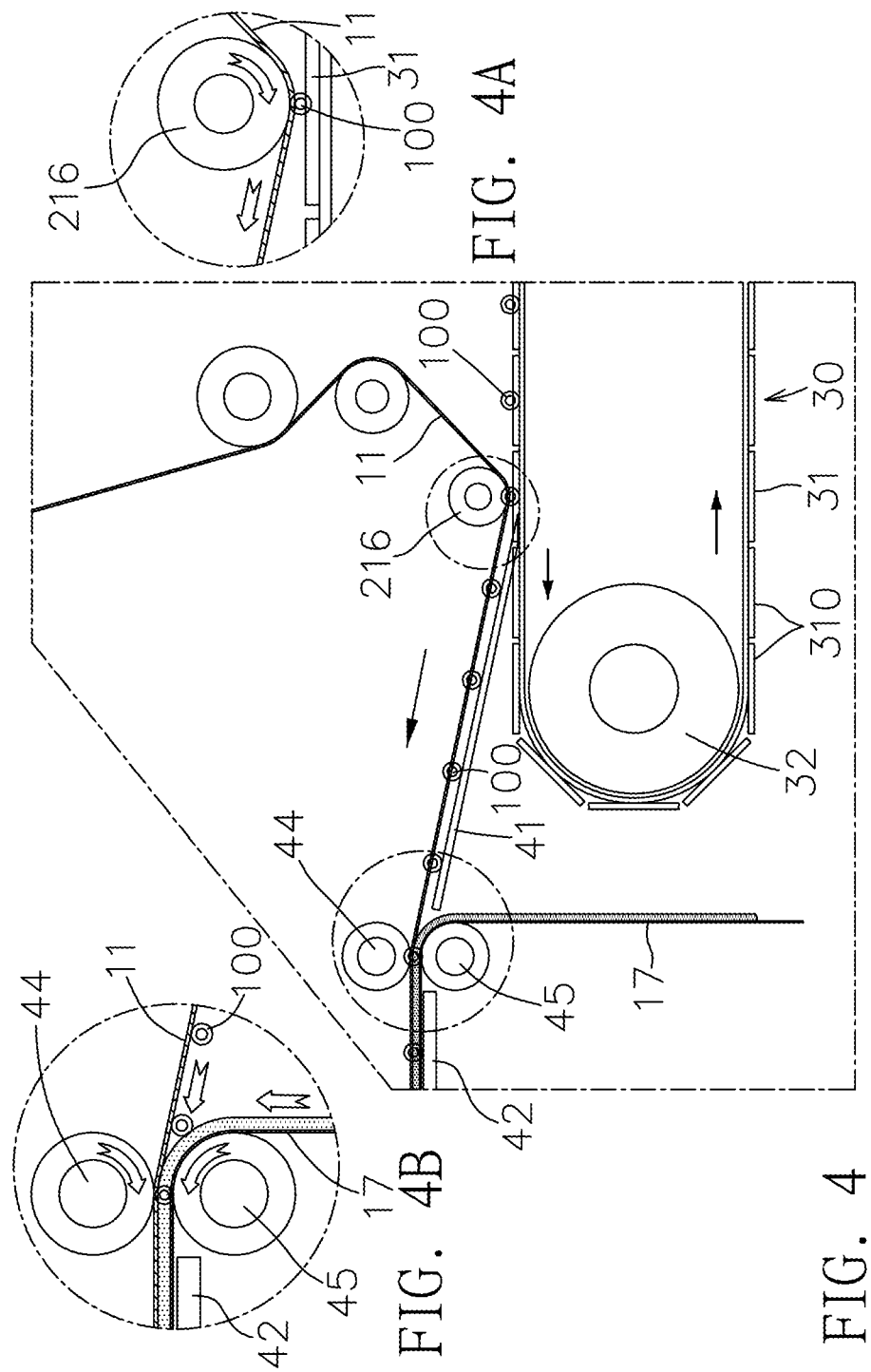

WIRING LOOP STRUCTURE OF SKIN ELECTRODE PAD PRODUCTION MACHINE

FIELD OF THE INVENTION

The present invention relates to a wiring loop structure of a skin electrode pad production machine, in particular to the structure providing the convenience and economic benefits for the assembling and manufacture of a skin electrode pad by arranging the installation of the electrode lead at an appropriate position.

BACKGROUND OF THE INVENTION

Description of the Related Art

Electrode treatment devices are generally used for the treatment of skin, the relief of various nervous and muscular pains, the stimulation of nerves and muscles, the adjustment of meridians, and the improvement of blood circulation. In addition, the electrode treatment devices are usually used together with a skin electrode pad, and the skin electrode pad is attached to a position of a human body to be treated, and a power supply and a circuit capable of outputting positive and negative current pulses are embedded into the skin electrode pad to form a seamless waterproof structure as a whole, and such devices with the skin electrode pad can be used as a self-adhesive pad for generating and outputting electrode pulses.

With reference to FIG. 1 for the assembly and manufacture of a conventional skin electrode pad, a skin electrode pad set 1 is comprised of a plurality of skin electrode pads 10, and each skin electrode pad 10 includes a clad substrate portion 11 and a conductive adhesive portion 17, wherein the clad substrate portion 11 has a clad body 12, and a side of the clad body 12 is adhered to an adhesive layer 13; the conductive adhesive portion 17 includes an adhesive layer body 14, and a side of the adhesive layer body 14 is adhered to a conductive layer 15, and the other side of the adhesive layer body 14 is attached to a release layer 16 (such as a release paper, etc). During assembling, the adhesive layer 13 of the clad substrate portion 11 is adhered to an electrode lead 100 first, or the electrode lead 100 is placed on the conductive adhesive portion 17 first, and then the clad substrate portion 11 and the conductive adhesive portion 17 are laminated and adhered, such that the electrode lead 100 is mounted between the clad substrate portion 11 and the conductive adhesive portion 17, and the electrode lead 100 and the conductive layer 15 are electrically conducted and coupled. Now, the electrode connector 101 of the electrode lead 100 is protruded to the outside as shown in the figure, and then the patterning and cutting processes are performed to form the skin electrode pad 10.

In the aforementioned method of assembling and manufacturing the skin electrode pad 10, the electrode lead 100 is installed on the clad substrate portion 11 or the conductive adhesive portion 17 and then laminated, so that the operation for positioning the electrode lead 100 onto the clad substrate portion 11 or the conductive adhesive portion 17 becomes cumbersome and time-consuming which is unfavorable to the speed improvement of a production line, and such method is obviously not a good method. In addition, the electrode lead 100 is set and positioned manually before the assembling process takes place, so that it is relatively difficult to set the electrode lead 100 into position precisely and thus giving rise to a different control of quality. Therefore, it is an important subject for related manufacturers to improve the drawbacks of the conventional skin electrode pad.

In view of the drawbacks of the conventional skin electrode pad and its manufacturing method, the inventor of the present invention conducted researches and experiments and finally developed a wiring loop structure of a skin electrode pad production machine with excellent convenience, efficiency and quality to overcome the drawbacks of the prior art.

SUMMARY OF THE INVENTION

Therefore, it is a primary objective of the present invention to provide a structure to facilitate the assembling and installation of an electrode lead in a skin electrode pad manufacturing process and provide an excellent efficiency and a highly stable quality.

Another objective of the present invention is to improve the conventional skin electrode pad manufacturing process that adheres the electrode lead manually electrode lead and to manufacture a skin electrode pad with the effects of secured positioning and convenient delivery.

To achieve the aforementioned and other objectives, the present invention discloses a technical measure comprising: a substrate transfer means, including a first transmission means for transmitting a strip clad substrate portion; a second transmission means for transmitting a strip conductive adhesive portion; a positioning conveyor including a circulation conveyor belt with a plurality of positioning fixtures installed thereon; and a fitting type cutting means installed at a following portion of the positioning conveyor and having two laminating rollers for laminating the clad substrate portion and the conductive adhesive portion; wherein the first transmission means includes an assembling roller disposed above an end of the circulation conveyor belt, and the positioning fixture is provided for positioning an electrode lead, and the strip clad substrate portion is adhered to the electrode lead by the assembling roller, and then the strip clad substrate portion and the conductive adhesive portion are attached after being laminated by the two laminating rollers.

Wherein, the positioning conveyor further includes a transmission wheel disposed at both ends of the circulation conveyor belt separately, and the circulation conveyor belt includes a plurality of conveyor belt plates pivotally coupled to each other.

Wherein, the conveyor belt plate the conveyor belt plate has at least one of the positioning fixtures.

Wherein, the circulation conveyor belt the circulation conveyor belt is a continuous flexible or bendable strip.

Wherein, the electrode lead has an electrode connector and an electrode terminal disposed at both ends of the electrode pad respectively, and the electrode terminal is embedded and positioned at the positioning fixture.

Wherein, the fitting type cutting means further includes a stripping guide plate slantingly coupled to an end portion of the positioning conveyor, and the front end of the stripping guide plate is configured to be corresponsive to the assembling roller.

Wherein, the fitting type cutting means further includes a receiving plate and a patterning wheel, and the receiving plate is installed at a following portion of the two laminating rollers, and the patterning wheel is installed above the receiving plate.

Wherein, the fitting type cutting means has a cutting means disposed at a rear portion of the fitting type cutting means, and the cutting means includes a cutting wheel.

Wherein, the cutting means has a product transmission means disposed at a rear portion of the cutting means, and the product transmission means includes a transmission portion.

Wherein, the clad substrate portion includes a clad body and an adhesive layer, and the conductive adhesive portion includes an adhesive layer body, a conductive layer and a release layer, and the electrode terminal of the electrode lead is adhered and coupled between the clad substrate portion and the conductive adhesive portion, and a lead connector is protruded from the outer side of the clad substrate portion and the conductive adhesive portion.

The above and other objects, features and advantages of this disclosure will become apparent from the following detailed description taken with the accompanying drawings.

BRIEF DESCRIPTION OF THE DRAWINGS

FIG. 4 is a schematic view of a fitting operation of the present invention;

FIG. 4A is a first partial schematic view of a fitting operation of the present invention; and FIG. 4B is a second partial schematic view of a fitting operation of the present invention.

DESCRIPTION OF THE PREFERRED EMBODIMENTS

Figure 1:
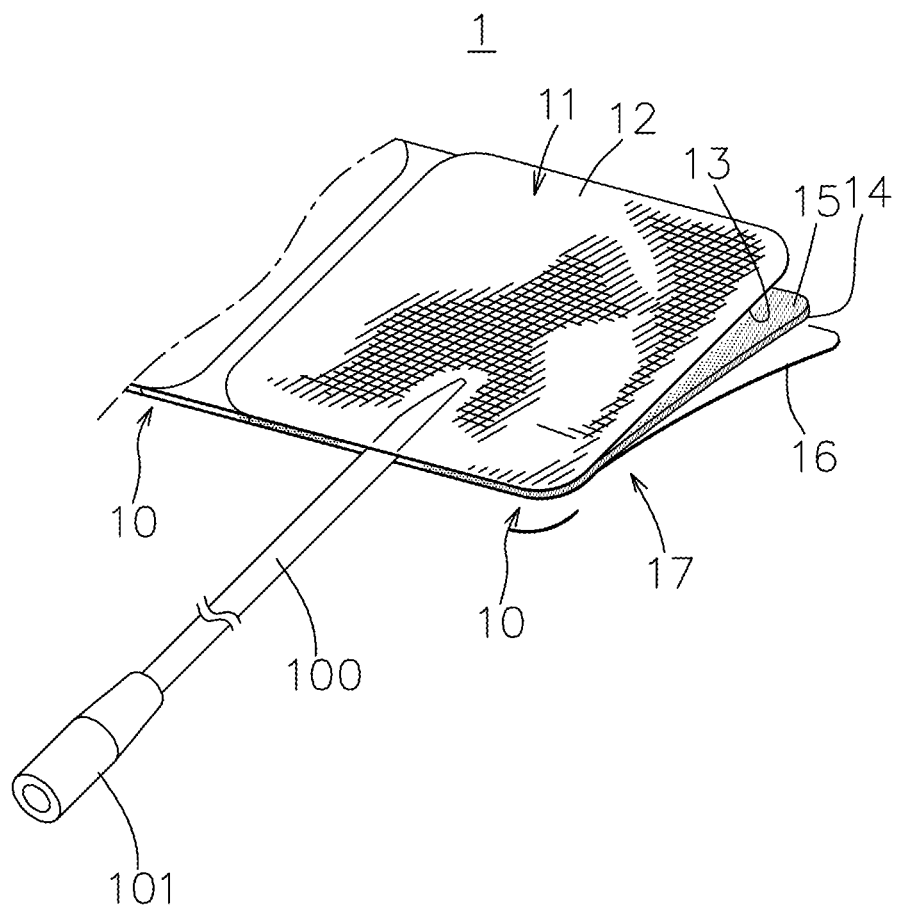
FIG. 1 is a schematic view of a manufactured assembly of a conventional skin electrode pad
Figure 2:
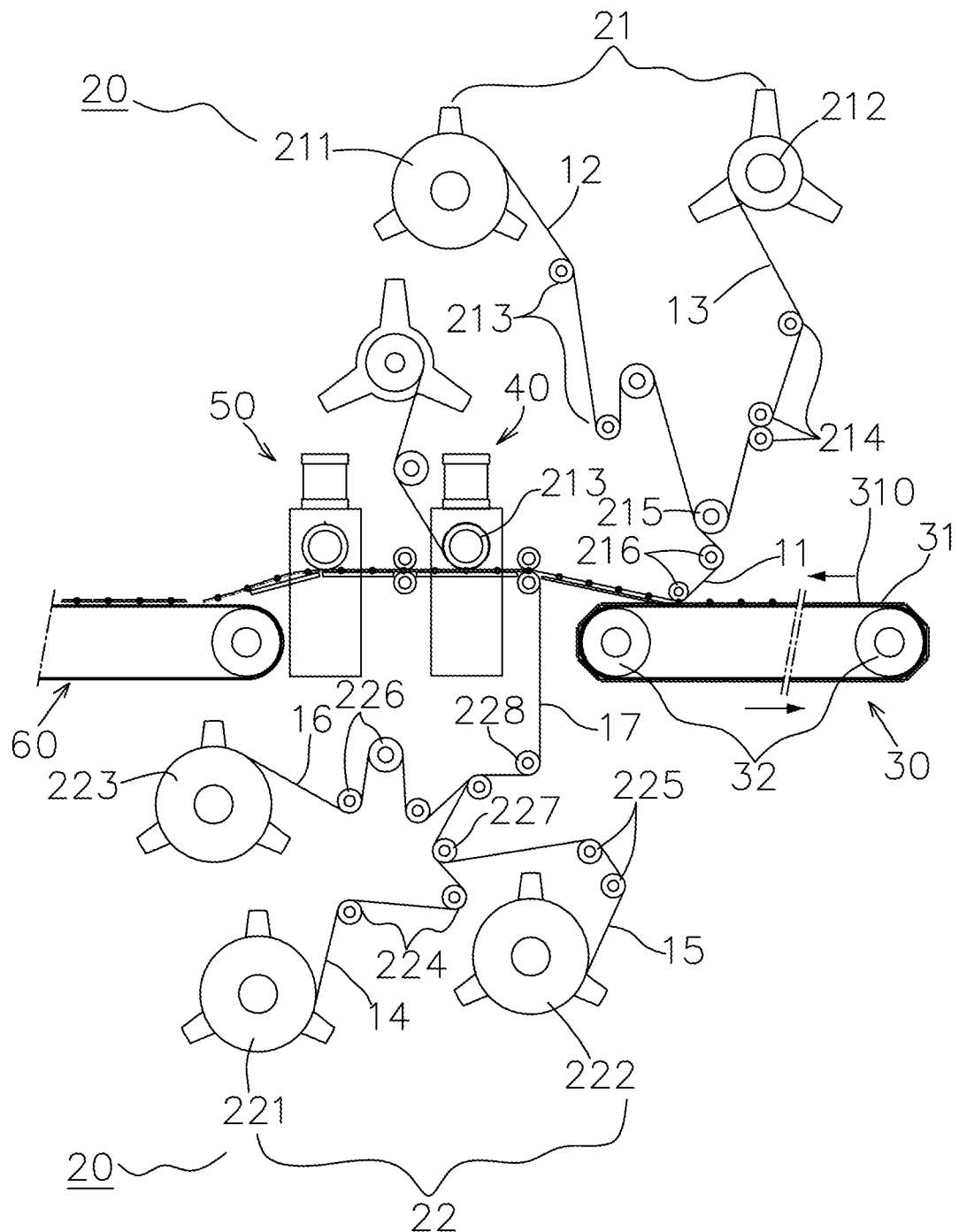
FIG. 2 is a schematic view of an operation flow of the present invention.
Figure 3:
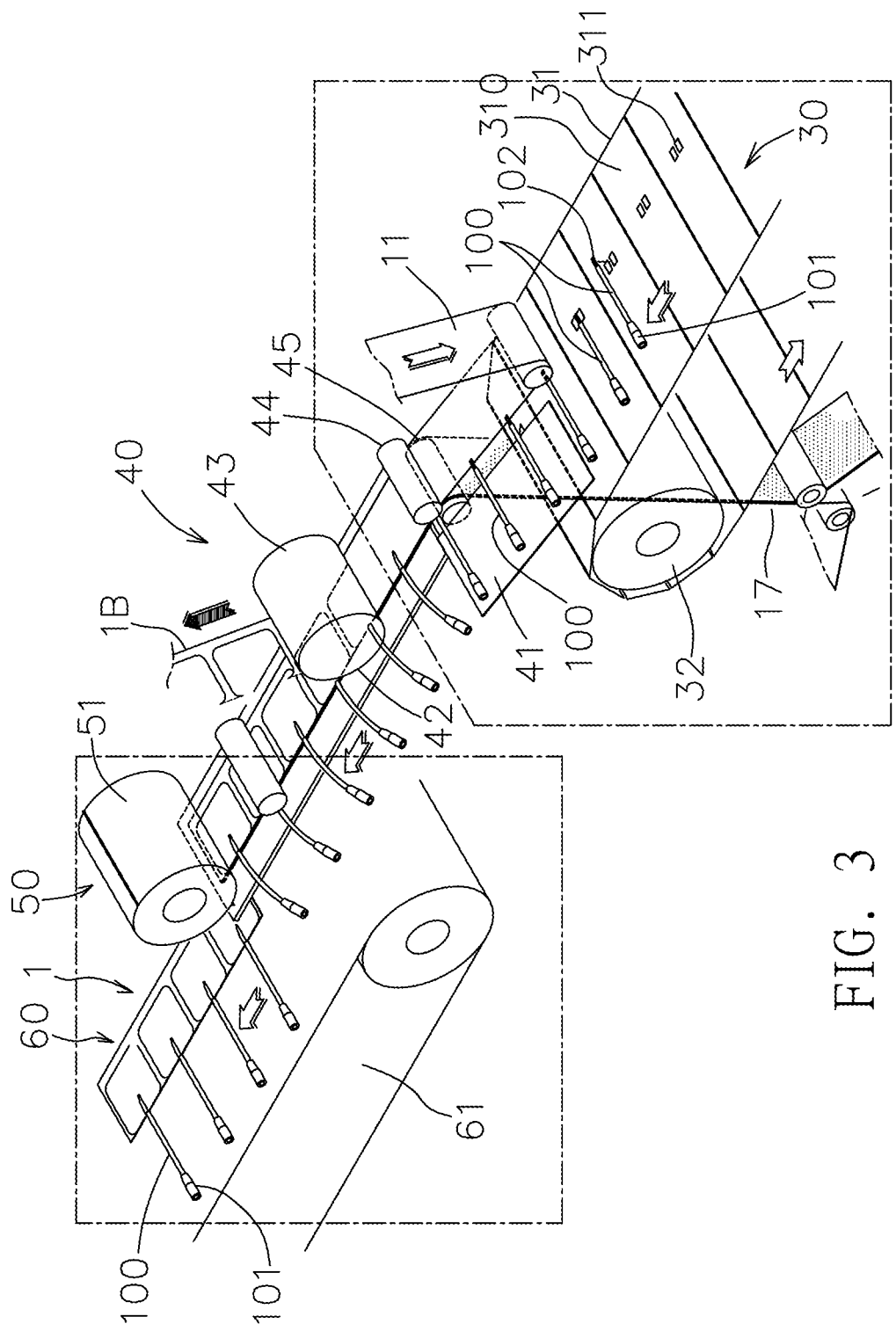
FIG. 3 is a schematic perspective view of an operation flow of the present invention.
Figure 3A:
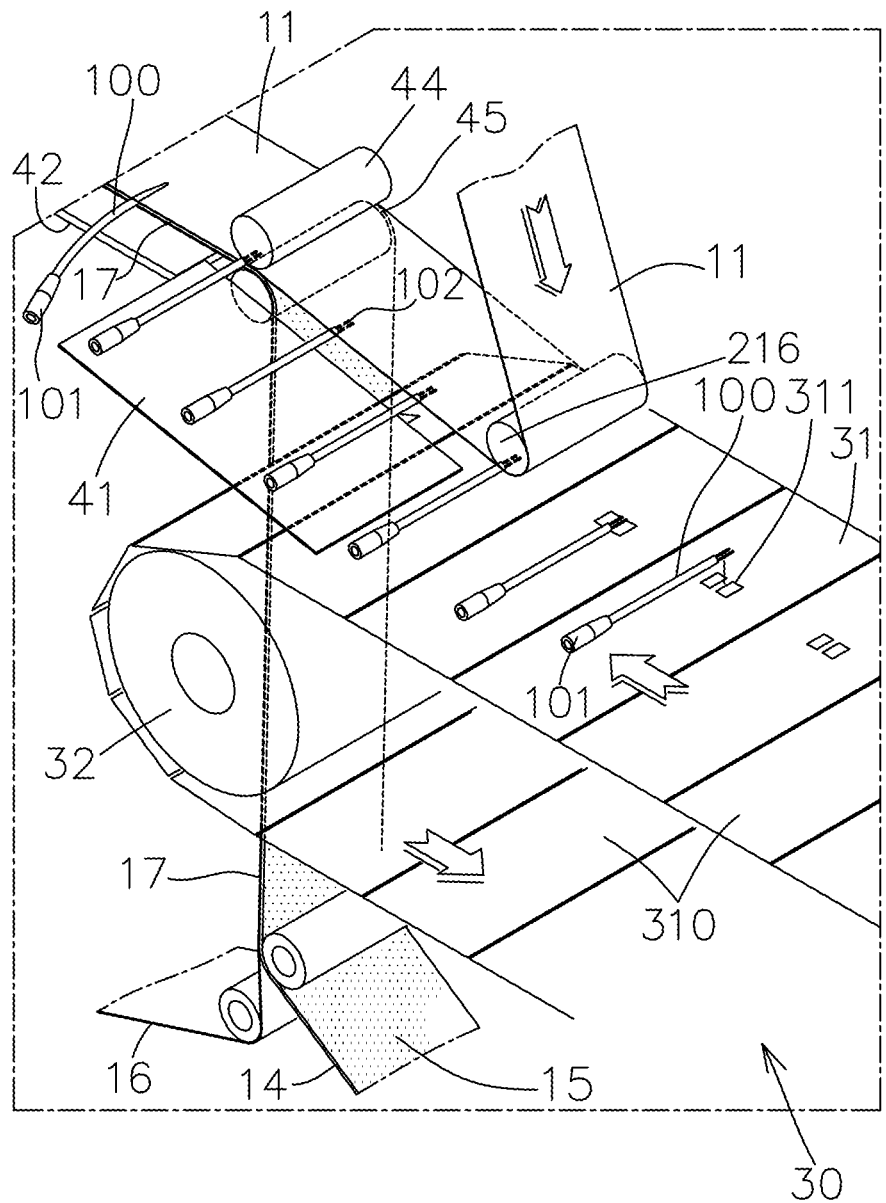
FIG. 3A is a partial schematic perspective view of an operation flow of the present invention.

With reference to FIGS. 2, 3 and 3A for the schematic views of a wiring loop structure of a skin electrode pad production machine of the present invention, it is noteworthy that these drawings are provided for illustrating the basic structure of the present invention but not necessarily drawn according to the actual shape, dimensions, and proportion for practical implementations of the invention. The wiring loop structure of the skin electrode pad production machine of the present invention s provided for assembling and manufacturing a skin electrode pad 10 (or a skin electrode pad set 1) as shown in FIG. 1, and the wiring loop structure comprises a substrate transfer means 20, a positioning conveyor 30, a fitting type cutting means 40, a cutting means 50 and a product transmission means 60, wherein the substrate transfer means 20 includes a first transmission means 21 and a second transmission means 22, and the first transmission means 21 includes two supply cylinders 211, 212 for supplying a strip clad body 12 and an adhesive layer 13. The strip clad body 12 is transmitted by a plurality of rollers 213, and the strip adhesive layer 13 is also transmitted by the plurality of rollers 214, and the strip clad body 12 and the adhesive layer 13 are attached by a fitting roller 215 to form a strip clad substrate portion 11, and the strip clad substrate portion 11 is transmitted by at least one assembling roller 216 to the positioning conveyor 30. The second transmission means 22 includes three supply cylinders 221, 222, 223 for supplying a strip adhesive layer body 14, a conductive layer 15, and a release layer 16 respectively. The strip adhesive layer body 14 is transmitted by a plurality of rollers 224, and the strip conductive layer 15 is transmitted by a plurality of rollers 225, and then the strip release layer 16 is transmitted by a plurality of rollers 226, and the strip adhesive layer body 14 and the conductive layer 15 are attached by a fitting roller 227, and then attached to the release layer 16 by a fitting roller 228 to form a strip conductive adhesive portion 17, and finally transmitted to the fitting type cutting means 40.

The positioning conveyor 30 includes a circulation conveyor belt 31 and two transmission wheels 32 disposed at both ends of the circulation conveyor belt 31 separately, and the transmission wheels 32 provide the power for moving the circulation conveyor belt 31 repeatedly, and the circulation conveyor belt 31 is formed by connecting a plurality of conveyor belt plates. Preferably, the conveyor belt plates are pivotally connected, so that two circulation conveyor belt plates 310 are connected with an appropriate curvature. In another embodiment, the circulation conveyor belt 31 may be a continuous flexible/bendable strip, but its shape is not limited to such arrangement only. In addition, the circulation conveyor belt 31 has a plurality of positioning fixtures 311, and in this embodiment, each conveyor belt plate 310 has a positioning fixture 311, so as to constitute the plurality of positioning fixtures 311 of the circulation conveyor belt 31. The positioning fixture 311 is used for positioning an electrode lead 100, and both ends of the electrode lead 100 have an electrode connector 101 and an electrode terminal 102 respectively. When the positioning conveyor 30 is assembled and used, the positioning fixture 311 is used to position the electrode lead 100, and in this embodiment, the electrode terminal 102 is embedded and position at the positioning fixture 311, so that the electrode lead 100 can be positioned on the conveyor belt plate 310 (or the circulation conveyor belt 31) and then moved and delivered accordingly.

With reference to FIGS. 4, 4A and 4B, the fitting type cutting means 40 is installed to a following portion of the positioning conveyor 30 and includes a stripping guide plate 41, a laminating roller 44, 45, a receiving plate 42 and a patterning wheel 43, wherein the stripping guide plate 41 is slantingly coupled to an end portion of the positioning conveyor 30, and the front end of the stripping guide plate 41 is configured to be corresponsive to an assembling roller 216 for transmitting the clad substrate portion 11. In the meantime, the assembling roller 216 is disposed above the rear end of the circulation conveyor belt 31, and the laminating roller 44, 45 is installed at a following portion of the stripping guide plate 41, and the receiving plate 42 is installed at a following portion of the laminating roller 44, 45, and the patterning wheel 43 is installed above an appropriate position of the receiving plate 42. The cutting means 50 is installed at a rear portion of the fitting type cutting means 4 and includes a cutting wheel 51. The product transmission means 60 is installed at a following portion of the cutting means 50 and includes a transmission portion 61.

In an application of a wiring loop structure of a skin electrode pad production machine of the present invention, the clad substrate portion 11 is dragged and pulled backward by a pulling force, and finally the clad substrate portion 11 enters into a position above the rear end of the circulation conveyor belt 31 from the assembling roller 216, so that the electrode lead 100 previously arranged on the circulation conveyor belt 31 can be attached onto the adhesive layer 13 of the clad substrate portion 11 (as shown in FIG. 4A), and then the clad substrate portion 11 is moved. In this embodiment, the electrode terminal 102 of the electrode lead 100 is adhered to the clad substrate portion 11 (or the adhesive layer 13), and then the clad substrate portion 11 enters into the stripping guide plate 41 and moves continuously. When reaching the laminating roller 44, 45, the clad substrate portion 11 is attached to the conductive adhesive portion 17. The conductive adhesive portion 17 is also dragged and pulled backward by a pulling force, and finally the conductive adhesive portion 17 enters from the laminating roller 45 into the receiving plate 42. Since the clad substrate portion 11 and the conductive adhesive portion 17 enter through the laminating roller 44, 45 into the receiving plate 42 of the fitting type cutting means 40, so that the clad substrate portion 11 and the conductive adhesive portion 17 are laminated and connected by the laminating roller 44, 45. Now, the electrode lead 100 (or the electrode terminal 102) is clamped and positioned between the clad substrate portion 11 and the conductive adhesive portion 17, and the electrode connector 101 is protruded from the outer side of the clad substrate portion 11 and the conductive adhesive portion 17. In this embodiment, the electrode terminal 102 of the electrode connector 101 is clamped and positioned between the clad substrate portion 11 and the conductive adhesive portion 17, and the reminder is protruded from the outer side of the clad substrate portion 11 and the conductive adhesive portion 17.

Now, the clad substrate portion 11 including the electrode lead 100 is stably attached, and the conductive adhesive portion 17 continuous to move at the receiving plate 42. When the conductive adhesive portion pass through the patterning wheel 43, the clad body 12 of the clad substrate portion 11 will be patterned and cut by the patterning wheel 43, and the patterned clad body remainder belt 1B is separated. After the patterning process, the cutting means 50 makes use of the cutting wheel 51 to cut the strip clad substrate portion 11 and the conductive adhesive portion 17 into strips, so as to complete the manufacture of the skin electrode pad set 1, and the skin electrode pad set 1 falls on the transmission portion 61 of the product transmission means 60 for the collection of the product.

The wiring loop structure of the skin electrode pad production machine of the present invention improves over the conventional skin electrode pad manufacturing process which adheres the electrode lead manually for assembling, and the invention assembles and manufactures provides a skin electrode pad with a stably positioned electrode lead and a more convenient transportation, and the product has the advantages of excellent assembling and manufacturing efficiency and highly reliable quality.

While the invention has been described by means of specific embodiments, numerous modifications and variations could be made thereto by those skilled in the art without departing from the scope and spirit of the invention set forth in the claims.

What is claimed is:

1. A wiring loop structure of a skin electrode pad production machine, comprising:
    a substrate transfer means, comprising:
        a first transmission means including two supply cylinders for supplying a strip clad body and a strip adhesive layer, a plurality of first rollers configured to transmit the strip clad body and the strip adhesive layer, and a first fitting roller configured to attach the strip clad body and the strip adhesive layer to form a strip clad substrate portion; and
        a second transmission means including three supply cylinders for supplying a strip adhesive layer body, a strip conductive layer and a strip release layer, respectively, a plurality of second rollers configured to transmit the strip conductive layer and the strip release layer, a second fitting roller configured to attach the strip adhesive layer body and the strip conductive layer, a third fitting roller configured to attach the strip adhesive layer body and the strip conductive layer to the release layer to form a strip conductive adhesive portion;
    a positioning conveyor, including a circulation conveyor belt and two transmission wheels disposed at both ends of the circulation conveyor belt separately, the transmission wheels providing the power for moving the circulation conveyor belt repeatedly, the circulation conveyor belt having a plurality of positioning fixtures installed thereon, each of the plurality of positioning fixtures configured to position an electrode lead, each of the plurality of positioning fixtures having two protrusions on a surface of the positioning conveyor, wherein ends of the electrode lead have an electrode connector and an electrode terminal respectively, wherein the electrode lead is part of the skin electrode pad, wherein the electrode terminal is embedded into one of the plurality of positioning fixtures and positioned at the one of the plurality of positioning fixtures so that the electrode lead can be positioned on the circulation conveyor belt;
    a fitting type cutting means, installed at a following portion of the positioning conveyor, the fitting type cutting means comprising:
        a stripping guide plate slantingly coupled to an end portion of the positioning conveyor;
        two laminating rollers installed at a following portion of the stripping guide plate for laminating the strip clad substrate portion and the strip conductive adhesive portion, after the strip clad substrate portion and the strip conductive adhesive portion are laminated by the laminating rollers, the electrode connector being disposed at an end of the electrode lead protruding from an outer side of the strip clad substrate portion and the strip conductive adhesive portion, the electrode terminal being coupled between the strip clad substrate portion and the strip conductive adhesive portion;
        a receiving plate installed at a following portion of the two laminating rollers; and
        a patterning wheel installed above the receiving plate; and
    an assembling roller disposed above a rear end of the circulation conveyor belt and configured to transmit the strip clad substrate portion to a position above the rear end of the circulation conveyor belt.

2. The wiring loop structure of a skin electrode pad production machine according to claim 1, wherein the circulation conveyor belt is a continuous flexible or bendable strip.

3. The wiring loop structure of a skin electrode pad production machine according to claim 1, wherein the fitting type cutting means has a cutting means disposed at a rear portion of the fitting type cutting means, and the cutting means includes a cutting wheel.

4. The wiring loop structure of a skin electrode pad production machine according to claim 3, wherein the cutting means has a product transmission means disposed at a rear portion of the cutting means, and the product transmission means includes a transmission portion, which is a conveyor for transporting product away from the cutting means.

\* \* \* \* \*